(12) United States Patent
Kelleher

(10) Patent No.: US 7,956,081 B2
(45) Date of Patent: Jun. 7, 2011

(54) PROCESS FOR CONTROLLING PROTEIN TO SALT RATIO IN ANIMAL MUSCLE PROTEIN COMPOSITION AND PROTEIN COMPOSITION

(75) Inventor: Stephen D. Kelleher, Ipswich, MA (US)

(73) Assignee: Proteus Industries, Inc., Gloucester, MA (US)

( * ) Notice: Subject to any disclaimer, the term of this patent is extended or adjusted under 35 U.S.C. 154(b) by 893 days.

(21) Appl. No.: 11/977,631

(22) Filed: Oct. 26, 2007

(65) Prior Publication Data

US 2008/0076150 A1    Mar. 27, 2008

Related U.S. Application Data

(60) Division of application No. 11/188,267, filed on Jul. 25, 2005, now abandoned, which is a continuation-in-part of application No. 10/655,604, filed on Sep. 5, 2003, now abandoned.

(60) Provisional application No. 60/464,614, filed on Apr. 23, 2003.

(51) Int. Cl.
  *C07K 1/14*    (2006.01)
(52) U.S. Cl. ........ 514/412; 514/414; 514/418; 514/422; 514/344; 426/657; 426/656
(58) Field of Classification Search .................. None
  See application file for complete search history.

(56) References Cited

U.S. PATENT DOCUMENTS 6,288,216 B1 *   9/2001   Hultin et al. .................. 530/412

* cited by examiner

*Primary Examiner* — Allison Ford
(74) *Attorney, Agent, or Firm* — Paul J. Cook

(57) ABSTRACT

A low salt protein solution not capable of forming a gel is obtained from animal muscle tissue by forming an aqueous acidic protein solution which is filtered to remove salt and acid. The low salt protein solution can be formed into a gel by adding a physiologically acceptable salt to the low salt protein solution and heating the resultant protein solution with added salt.

21 Claims, No Drawings

PROCESS FOR CONTROLLING PROTEIN TO SALT RATIO IN ANIMAL MUSCLE PROTEIN COMPOSITION AND PROTEIN COMPOSITION

REFERENCE TO RELATED APPLICATION

This application is a divisional application of application Ser. No. 11/188,267, filed Jul. 25, 2005 now abandoned which in turn is a continuation-in-part application of application Ser. No. 10/655,604, filed Sep. 5, 2003 now abandoned which, in turn, is based on provisional application Ser. No. 60/464,614, filed Apr. 23, 2003.

BACKGROUND OF THE INVENTION

This invention relates to a process for making an edible functional animal muscle protein concentrate composition and to a process for making the composition wherein gelation of the composition is controlled. More particularly, this invention relates to a process for making the functional animal muscle protein concentrate from animal muscle tissue wherein gelation of the composition is controlled so that its gelation is effected when it is used such as by being added to a food.

Prior to the present invention, protein compositions derived from animal muscle tissue have been available for human consumption as disclosed in U.S. Pat. Nos. 6,005,073; 6,288,216 and 6,451,975 as well as U.S. patent application Ser. No. 10/161,171, filed Jun. 4, 2002. Unfortunately, the liquid form of these compositions form gels at a time after they are initially formed which is temperature-dependant. The higher the composition temperature, the shorter the time needed to form the gel. Gel formation of these compositions causes processing problems in that the gel clogs the processing equipment to the point that the composition can not be moved through the processing equipment. In addition, since gel formation is quicker at elevated composition temperature, the composition cannot be pasteurized with heat while maintaining the composition as a liquid. This result is undesirable since oftentimes the composition requires pasteurization prior to consumption by humans.

Prior to the present invention, it has been known that meat or fish cooked at an elevated temperature loses its moisture to the surrounding atmosphere. In so doing, the cooked meat or fish undesirably loses its natural or added flavors so that it becomes less tasteful. Fluid loss during cooking of meat or fish can range up to 30% to 40% by weight based upon the weight of the meat or fish prior to cooking. A prior solution for retaining moisture in the meat or fish without additives took the form of wrapping the meat or fish in a solid moisture barrier such as aluminum foil. This solution is undesirable since the surface of the meat or fish remains soft rather than having a desirable crust.

Food additives also have been used to retain moisture in cooked meat or fish. Representative additives include sodium tripolyphosphate, a coating of fat free flour, based, batter containing an egg white substitute (U.K. Patent Application 2,097,646), water-in-oil emulsion (U.S. Pat. No. 3,406,081), protein or protein isolate and a fat (U.S. Pat. Nos. 4,031,261 and 4,935,251), milk solids (U.S. Pat. No. 2,282,801) and lecithin (U.S. Pat. Nos. 2,470,281 and 3,451,826).

Accordingly, it would be desirable to provide a process for producing an edible protein composition derived from animal muscle tissue which can be pasteurized with heat without forming a gel of the composition. Furthermore, it would be desirable to provide such a process wherein the edible pasteurized protein composition can be treated so that it is capable of forming a gel. Such a process would permit pasteurizing the edible protein composition with heat followed by adding it to a food, for example, to effect moisture retention in the food during cooking or to improve the nutritional value of the food.

SUMMARY OF THE INVENTION

In accordance with this invention, a concentrated protein solution derived from animal muscle tissue is provided which is in the form of an "aqueous acidic protein solution" as defined below. In accordance with this invention, a process is provided whereby a concentrated aqueous acidic protein solution is isolated while controlling protein concentration in the solution as well as the weight ratio of protein concentration in the solution so that premature gelation of the solution is avoided. Premature gelation is avoided when the weight ratio of protein to salt in the aqueous acidic protein solution is above about 35 and the protein concentration is above about 1.9 weight percent. The weight ratio of protein to salt can be controlled either by adding protein or removing salt from the aqueous acidic protein solution. In one embodiment of this invention, an aqueous acidic protein solution is filtered to produce a retentate. The retentate is referred to herein as the "low salt protein solution" since salt dissolved in aqueous solution comprises the permeate that is separated from the retentate. The low salt protein solution does not form a gel when heated to a temperature of 55° C. or lower. In contrast, the aqueous acidic protein solution quickly forms a gel when heated to about 35° C. and forms a gel over time within a temperature range of about 4-30° C. or higher. In a second embodiment of this invention, protein derived from animal muscle tissue is added to the aqueous acidic protein solution to obtain the desired minimum protein concentration and the desired weight ratio of protein to salt whereby the resultant "low salt protein solution" does not form a gel at 55° C. or lower. When salt is added subsequently to the low salt protein solution up to physiological salt concentration (0.86 weight % salt), the resultant solution referred to herein as the "protein solution with added salt" is capable of forming a gel at room temperature or higher, e.g., 30-40° C. Gelation of the protein solution with added salt can be effected at room temperature or with heating whenever gelation is accelerated by heating it. This process for controlling gelation of the protein containing solution permits pasteurizing by heating the protein solution while avoiding gelation. Thus, because the protein solution has been pasteurized, it need not be subsequently pasteurized aft it has been added to a food. This control of protein gelation permits addition of the protein to foods which need not be cooked to improve the nutritional value of the food. In addition, direct safe ingestion of the protein is permitted.

The "aqueous acidic protein solution" is derived from animal muscle tissue and comprises an acidic solution comprising a mixture of myofibrillar proteins and sarcoplasmic proteins obtained by one of the processes disclosed in U.S. Pat. Nos. 6,005,073; 6,288,216; and/or 6,451,975 and/or U.S. patent application Ser. No. 10/161,171, filed Jun. 4, 2002 all of which are incorporated herein by reference in their entirety. In one embodiment of this invention, the low salt protein solution of this invention is obtained from the aqueous acidic protein solution by subjecting the aqueous acidic protein solution to filtration, including microporous filtration (microfiltration), ultrafiltration, or diafiltration while retaining a concentrate protein mixture containing myosin protein and actin protein in the recovered retentate. The retentate comprises the low salt protein solution, higher protein concentration solution of this invention. The low salt protein solution has a higher weight ratio of protein to salt as compared to the aqueous acidic protein solution comprising the feed to the filtration step. In addition, it contains a high concentration of protein than the aqueous acidic protein solution. The low salt protein solution comprises above about 1.9%, preferably above about 4% up to about 25% by weight protein based on the weight of the solution. Filtration of the aqueous acidic protein solution to form the low salt protein solution is conducted under conditions to remove salt from the solution so that the resultant low salt protein solution retentate does not form a gel even when heated up to 55° C. In a second embodiment, protein derived from animal muscle tissue and capable of forming a gel is added to the aqueous acidic protein solution to form a low salt protein solution that does not form a gel even when heated up to 55° C. Thus, the low salt protein solution can be pasteurized by heating at a temperature above about 70° C. up to the boiling temperature of the solution without forming a gel. If desired, the low salt protein solution also can be pasteurized by other conventional means such as with radiation.

Pasteurization is the process whereby a target organism is inactivated by heating. Representative microorganisms that can be inactivated include *listeria, salmonella, E. coli,* or the like.

In an alternative embodiment of this invention, the protein can be first isolated from animal muscle tissue by the process of U.S. Pat. No. 6,136,959 which is incorporated herein by reference to form an alkaline protein solution having a pH above about 10. The pH of the solution then is induced to a pH less than about 3.5 with a physiologically acceptable acid such as phosphoric acid and/or citric acid. The thus formed aqueous acidic solution then is treated by filtration or protein addition in the manner described above to effect the desired weight % Protein to weight % Salt ration (P/S) set forth above.

The "low salt protein solution" comprises a concentrated aqueous solution of myofibrillar proteins and sarcoplasmic proteins derived from animal muscle tissue and having a pH of 3.5 or less and preferably between about 2.5 and about 3.5 but not so low as to adversely affect the protein functionality. The low salt protein solution contains a weight % Protein to weight % Salt ratio (P/S) of greater than about 35, preferably greater than about 50. When it is desired to utilize the low salt protein solution as a food additive capable of forming a gel, salt is added to the low salt protein solution to effect a protein to salt weight ratio lower than about 35 at which the protein solution with added salt forms a gel at 40° C. or lower. The "low salt protein solution" can be pasteurized by any conventional means such as by heating or by radiation. When it is desired to utilize the low salt protein solution as a food additive not capable of forming a gel such as to soup, a fruit juice or to baby formula, no salt is added to the low salt protein solution.

The protein solution with added salt can be injected into a food such as fish or meat or it can be applied to the surface of the food or it can be mixed with the food. The food containing the protein solution with added salt then can be cooked at elevated temperature in the absence of a solid moisture barrier while retaining a substantial majority of its original moisture. The difference in weight between meat and fish treated in accordance with this invention compared with fish or meat not injected, mixed or coated with the protein solution with added salt is between about 4 and about 21%, more usually, between about 4 and about 10%. Also, in accordance with this invention, it has been found that the addition of the protein solution with added salt to food such as fish or meat provides a preservative effect in that it reduces microbial degradation of the fish or meat. The protein solution with added salt also can be utilized to restrict absorption by food of oil and/or fat used to cook the food. The protein solution with added salt can be applied to the surface of the food or it can be mixed with the food. The food containing the protein then can be cooked in liquid oil and/or fat at elevated temperature while minimizing absorption of oil and/or fat by the food. The difference in weight between food treated in accordance with this invention after being cooked in oil and/or fat compared with food not mixed or coated with the protein after being cooked in oil and/or fat is between about 10 and about 60%, more preferably between about 30 and about 60%. In addition, since the amount of absorbed fat or oil utilized during cooking is substantially reduced, the amount of oil or fat needed to cook a given weight of food is correspondingly substantially reduced.

DESCRIPTION OF SPECIFIC EMBODIMENTS

In accordance with this invention, a myosin-rich and actin-rich concentrated protein composition derived from animal muscle is provided in the form of an aqueous low salt protein solution. The composition of this invention is referred to herein as "low salt protein solution". The low salt protein solution can contain cholesterol or be free of cholesterol. In addition, in accordance with this invention, animal muscle tissue to be cooked is coated, admixed and/or injected with the low salt protein solution to which salt has been added so that the resultant solution can be converted to a gel at a temperature of about 40° C. or lower. The composition of this invention comprises a mixture of myofibrillar proteins and sarcoplasmic proteins derived from animal muscle tissue and obtained from the aqueous acidic protein solution formed by the processes disclosed in U.S. Pat. Nos. 6,005,073, 6,288,216, and 6,451,975 and application Ser. No. 10/161,171, filed Jun. 4, 2002 followed by filtration with a microporous, ultrafiltration or diafiltration membrane of the aqueous acidic protein solution to recover the retentate in one embodiment of this invention. The retentate is obtained under filtration conditions to recover a protein composition in the retentate that includes myosin protein and actin protein and which has a protein concentration of about 1.9% or higher and a sufficiently high weight ratio of protein to salt (greater than about 35) so that it does not gel at room temperature or when heated to a temperature of 55° C. The retentate comprises one embodiment of the low salt protein solution of this invention. During filtration, acid and/or salt passes through the filter into the permeate. In diafiltration, water is added to the protein solution to be filtered in order to carry salts and/or acid through the filter into the permeate. Water addition is ceased and filtration is continued to reduce the water in the retentate.

The aqueous acidic protein solution which is subsequently filtered is obtained by one of two processes. In these processes, (acid processes) animal muscle tissue is formed into small tissue particles which are then mixed with sufficient acid to form a solution of the tissue having a pH of 3.5 or less, but not such a low pH as to adversely modify the animal tissue protein, e.g., about 1.0 or less. In one of these two processes, the solution is centrifuged to form a lowest membrane lipid layer, an intermediate layer of aqueous acidic protein solution and a top layer of neutral lipids (fats and oils). The intermediate layer of aqueous acidic protein solution is then separated from the membrane lipid layer or from both the membrane lipid layer and the neutral lipid layer. In a second of these two processes, the aqueous acidic protein solution is recovered without a centrifugation step since the starting animal muscle tissue contains low concentrations of undesired lipids, oils and/or fats. In both processes, the protein mixture is free of myofibrils and sarcomeres. In both processes, the aqueous acidic protein solution is filtered to recover a myosin-rich and actin-rich retentate which comprises the low salt protein solution of this invention and to form a permeate comprising an aqueous acid/and or salt solution which may or may not contain cholesterol. The low salt protein solution of this invention contains above about 1.9 wt. % protein, more usually above about 4 wt. % protein to about 25 wt. % protein based on the weight of low salt protein solution and can be utilized with added salt with food such as uncooked meat or fish. The recovered low salt protein solution then can be mixed with added salt to obtain a protein solution that can form a gel when heated to a temperature of 30-40° C. The mixture of the low salt protein solution and added salt then can be injected into or coated on or mixed with food such as fish or meat to be cooked or to be preserved.

In one embodiment, the low salt protein can be pasteurized such as by heating or with radiation and then it can be dried such as by spray drying, freeze drying and/or evaporation to form a pasteurized protein powder. The dry powder can be dissolved in water when desired.

In an alternative embodiment of this invention, the protein can be first isolated from animal muscle tissue by the process of U.S. Pat. No. 6,136,959 which is incorporated herein by reference to form an alkaline protein solution having a pH above about 10. The pH of the solution then is induced to a pH less than about 3.5 with a physiologically acceptable acid such as phosphoric acid and/or citric acid. The thus formed aqueous acidic solution then is treated by filtration or protein addition in the manner described above to effect the desired weight % Protein to weight % Salt ration (P/S) set forth above.

Filtration can be effected by microporous filtration, ultrafiltration or diafiltration. Microporous filtration can be effected with a water wettable microporous membrane such as a membrane designed to retain particles having an average size between about 0.01 and 5 microns. Ultrafiltration can be effected with a water wettable membrane designed to retain particles having an average size between about 0.001 and about 0.02 microns.

Ultrafiltration is effected with a water wettable ultrafiltration membrane having a molecular weight cut-off which effects retention of myosin heavy chain protein (~205,000 Daltons) and actin protein (~42,000 Daltons). Representative suitable ultrafiltration membranes have a molecular weight cut-off between about 3,000 Daltons and about 100,000 Daltons, preferably between about 10,000 Daltons and about 50,000 Daltons. Ultrafiltration membranes having a molecular weight cut-off above 42,000 Daltons can be utilized to retain myosin and actin since the acidic conditions of the solution cause the protein to unfold thereby promoting their retention by the ultrafiltration membranes. Ultrafiltration can be effected by tangential flow filtration (TFF) with a single pass or with multiple passes over the ultrafilter. The retentate recovered during filtration comprises the low salt protein solution of this invention, which can be pumped, heat pasteurized and stored as a liquid for subsequent mixture with a salt or can be mixed with a salt to form a solution which can be formed into a gel when heated above about 30-40° C. The low salt protein solution of this invention comprising the retentate has reduced water concentrations, possibly reduced cholesterol concentrations and possibly reduced low molecular weight protein concentrations, as compared to the aqueous acidic protein solution obtained prior to filtration. The low salt protein solution of this invention contains between about 1.9 and about 25 weight percent protein, preferably between 4 and 12 weight percent protein and a weight % Protein to weight % Salt ratio (P/S) of greater than about 35, preferably greater than about 50. Filtration also can be effected with a diafiltration membrane which permits passage there-through of water or an aqueous acid and/or salt solution, and possibly cholesterol while retaining proteins. Representative suitable membranes include, polyethersulfones, polyamides, polycarbonates, polyvinylchloride, polyolefins such as polyethylene or polypropylene, cellulose esters such as cellulose acetate or cellulose nitrate, regenerated cellulose, polystyrene, polyimides, polyetherimides, acrylic polymers, methacrylic polymers, copolymers thereof, blends thereof or the like.

To determine whether a low salt protein solution of this invention or a mixture of the low salt protein solution and added salt can form a gel when heated, it is tested as follows:

Approximately 20 ml of protein solution is placed on a paper plate, swirled to disperse it. It is then microwaved for 15 seconds on high in a 1000 W microwave. The resulting cooked product is inspected for coagulation, water binding ability and prodded for elasticy. A product considered to gel will bind all available water, and form a highly elastic gel. A non-gelling product would remain a free-flowing liquid.

In a second embodiment of this invention, protein derived from animal muscle tissue is added to the aqueous acidic protein solution to form the low salt protein solution of this invention. The added protein is obtained by the process disclosed in U.S. Pat. Nos. 6,005,073; 6,288,216 and 6,451,975 as well as U.S. patent application Ser. No. 10/161,171, filed Jun. 4, 2002, all of which are incorporated herein by reference. This added protein is recovered by removing aqueous solution containing salt from precipitated protein. The precipitated protein comprises the protein added to the low salt protein solution.

The low salt protein solution of this invention is mixed with a salt such as in crystalline form or in aqueous solution in an amount to form a solution which forms a gel at 40° C. or below. The resulting solution can be applied alone or in admixture with conventional food or nutritive additives such as breading or batter coatings, spice dry rubs, cracker meal, corn meal, spices, flavorings, sugar, salt, pepper or the like. It is preferred to utilize the protein solution obtained from the low salt protein solution and added salt, with or without food or nutritional additives, for injection. The protein solution contains added salt and can be coated on the surface of the food such as meat or fish with an applicator or can be coated by tumbling the food such as meat or fish in the protein solution with added salt or in a marinade containing the protein solution with added salt in a tumbling or vacuum tumbling apparatus. Alternatively, when it is desired that protein added to food not form a gel even when heated to boiling temperature, such as in a soup, fruit juice or in baby formula, the protein is added to the food in the form of the low salt protein solution in accordance with this invention, In summary, the aqueous acidic protein solution utilized in the present invention to form the low salt protein solution can be obtained by the following preferred methods:

1. Reduce the pH of comminuted animal muscle tissue to a pH less than about 3.5 to form an acidic protein solution, centrifuge the solution to form a lipid-rich phase and an aqueous phase, recovering a aqueous acidic protein solution substantially free of membrane lipids and filtering the aqueous acidic protein solution to isolate the retentate comprising the low salt protein solution that can be used with added salt to form the protein solution with added salt.

2. Increase the pH of the aqueous acidic protein solution from method 1 to about pH 5.0-5.5 to effect precipitation of the proteins and then readjust the protein back to a pH of about 3.5 or less using a physiologically acceptable acid in a minimum volume to concentrate the aqueous acidic protein solution to between 3.5-7% protein and filtering the aqueous acidic protein solution to recover the low salt protein solution as retentate.

3. Reduce the pH of comminuted animal muscle tissue to form an aqueous acidic protein solution which is filtered to produce the low salt protein solution of this invention. The low salt protein solution is mixed with salt to form the protein solution with added salt that can be converted to a gel when heated to a temperature of 40° C.

Alternatively, in methods 4, 5 and 6, methods 1, 2 and 3 can be modified by replacing the filtration step with a step of adding a solid or gel protein from animal muscle tissue obtained by a method disclosed in U.S. Pat. Nos. 6,005,073; 6,288,216 and 6,451,975 as well as U.S. patent application Ser. No. 10/161,171, filed Jun. 4, 2002 to the aqueous acidic protein solution to form the low salt protein solution.

Salt is added to the solution prepared by methods 1, 2, 4, 5 or 6 to form a protein solution that forms a gel either at room temperature or when heated to a temperature of 30-40° C. Salt is added in aqueous solution or as crystals, preferably in aqueous solution since instant gelling of the resulting solution is more easily avoided. By avoiding instant gelation caused by salt addition, sufficient time is provided to transport the resulting protein solution to a point of use such as the addition of the resulting protein solution to a food. Any physiologically acceptable salt can be utilized such as sodium or potassium salts including citrates, chlorides, phosphates or the like.

The protein products utilized in the present invention comprise primarily myofibrillar proteins that also contain significant amounts of sarcoplasmic proteins. The sarcoplasmic proteins in the protein product admixed with, injected into or coated on the food comprises above about 6%, preferably above about 8%, more preferably above about 12% and most preferably above about 15%, up to about 30% by weight sarcoplasmic proteins, based on the total weight of protein in the dry acidic protein mixture or aqueous acidic protein solution.

In accordance with this invention the protein solution comprising myofibrillar proteins and sarcoplasmic proteins with added salt can be applied to the surface of food to be cooked, or is mixed with the food to be cooked such as hamburger, sliced reformulated beef or sausage. The term "a surface" as used herein is a surface of the food such as fish or meat which is positioned 90 degrees from an adjacent surface or surfaces of the meat or fish. In addition, the term "a surface" can comprise the connecting surface connecting two adjacent surfaces positioned 90 degrees from each other. Preferably, the entire surface of the food such as meat or fish is coated with the protein solution with added salt. The coated food such as fish or meat then can be cooked at elevated temperature while retaining a substantial majority of its original moisture.

In one aspect of this invention, particulate food such as ground meat or fish, e.g. hamburger, can be mixed with the protein solution comprising myofibrillar proteins and sarcoplasmic proteins with added salt at a weight ratio usually comprising about 0.03% to about 15% weight of the protein based on the weight of the uncooked food, preferably between about 0.5 and 5% weight based on the weight of uncooked food and most preferably comprising between about 0.5 to about 2% weight based on the weight of the uncooked food. When the protein solution with added salt is applied to at least one surface of the food or it is applied by injection, the amount of the protein mixture added is the same weight ratio as set forth above when mixed with ground meat or fish. When utilizing less than about 0.03% weight protein solution with added salt, effective moisture retention is not observed. When utilizing greater than about 15% protein solution with added salt, the cooked food can become undesirably hard.

It has also been found in accordance with this invention that the addition of the protein solution with added salt to uncooked fish or meat provides an unexpected preservative effect in that it reduces degradation by microbes to the food. It is preferred that the protein solution with added salt be applied to the surface of the food in order to provide this preservation effect.

The animal muscle tissue which is modified in accordance with this invention comprises meat and fish, including shell fish. Representative suitable fish include deboned flounder, sole, haddock, cod, sea bass, salmon, tuna, trout or the like. Representative suitable shell fish include shelled shrimp, crabmeat, crayfish, lobster, scallops, oysters, or shrimp in the shell or the like. Representative suitable meats include ham, beef, lamb, pork, venison, veal, buffalo or the like; poultry such as chicken, mechanically deboned poultry meat, turkey, duck, a game bird or goose or the like either in fillet form or in ground form such as hamburger. The meats can include the bone of the animal when the bone does not adversely affect the edibility of the meat such as spare ribs, lamb chops or pork chops. In addition, processed meat products which include animal muscle tissue such as a sausage composition, a hot dog composition, emulsified product or the like can be coated, injected or mixed with the protein solution with added salt, or a combination of these protein addition methods. Sausage and hot dog compositions include ground meat or fish, herbs such as sage, spices, sugar, pepper, salt and fillers such as dairy products as is well known in the art.

The fish or meat containing the protein solution with added salt then can be cooked in a conventional manner such as by baking, broiling, deep fat frying, pan frying, in a microwave oven or the like. It has been found that the cooked food provided in accordance with this invention weighs between about 4% and about 21%, more usually between about 4% and about 9% by weight greater than cooked untreated food starting from the same uncooked weight.

In one aspect of this invention, the protein solution with added salt restricts absorption of cooking oil and/or fat by food being cooked in the oil and/or fat. For example, particulate food such as ground meat or fish, e.g., hamburger, or a food mixture such as a pastry for doughnuts is mixed with the protein solution with added salt at a weight ratio usually comprising about 0.03 to about 18% weight of the protein solution with added salt based on the weight of the uncooked food, preferably between about 0.5 and 10% weight based on the weight of the uncooked food. When utilizing less than about 0.03% weight of the protein solution with added salt, prevention of oil and/or fat absorption is not observed. When utilizing greater than about 15% weight of the protein solution with added salt, the uncooked food can become undesirably hard.

Suitable oils and/or fats, including hydrogenated or non-hydrogenated oils which can be utilized to effect cooking of uncooked food are those conventionally used in cooking including lard, peanut oil, corn oil, vegetable oil, canola oil, palm oil, sesame oil, butter, mixtures thereof or the like.

The uncooked food which is modified in accordance with this invention comprises meat, poultry and fish, including shell fish, vegetables, tempura; nuts, mushrooms, flour based foods such as batter compositions, pastry compositions, chicken or the like. Representative suitable fish include deboned flounder, sole, haddock, cod, sea bass, salmon, tuna, trout or the like. Representative suitable shell fish include shelled shrimp, crabmeat, crayfish, lobster, scallops, oysters, or shrimp in the shell or the like. Representative suitable meats include ham, beef, lamb, pork, venison, veal, buffalo or the like; poultry such as chicken, mechanically deboned poultry meat, turkey, duck, a game bird or goose or the like either in fillet form or in ground form such as hamburg. The meats can include the bone of the animal when the bone does not adversely affect the edibility of the meat such as spare ribs, lamb chops or pork chops. In addition, processed meat products which include animal muscle tissue such as a sausage composition, a hot dog composition, emulsified product or the like can be coated or mixed with the protein solution with added salt, or a combination of these protein addition methods. Sausage and hot dog compositions include ground meat or fish, herbs such as sage, spices, sugar, pepper, salt and fillers such as dairy products as is well known in the art. Representative vegetables include potato, carrot, cauliflower, onion, corn or the like. Additional foods include mushroom, nuts, batter compositions such as those comprising flour, egg and milk which can include additional food such as cornmeal, cracker meal or dusting meals.

The food containing the protein solution with added salt then can be cooked with oil and/or fat in a conventional manner such as by deep fat frying, pan frying, or the like. It has been found that the uncooked food provided in accordance with this invention contains between about 10% and about 60%, preferably between about 30% and about 60% less oil/and/or fat by weight as compared to the same uncooked food free of the protein composition of this invention. The amount of fat or oil needed to cook a given weight of a given type of food also is correspondingly reduced.

In one aspect of this invention, it has been found that the addition of ethanol to the protein solution with added salt or to a coating such as a batter containing the protein solution with added salt results in a further reduction of fat and/or oil in food cooked in fat and/or oil as compared to the addition of the protein solution with added salt without ethanol. The concentration of ethanol for which this effect is observed is between about 0.5 and about 5% by weight, preferably between about 1% and about 5% by weight based on the total weight of batter, added protein solution with added salt and ethanol.

The following example illustrates the present invention and is not intended to limit the same.

The invention claimed is:

1. A process for recovering a low salt protein solution derived from animal muscle tissue, said solution being characterized as containing between about 1.9 and 25 weight % protein based on the weight of the solution, having a protein to salt weight ratio greater than about 35, and wherein said solution does not form a gel when heated to a temperature of 55° C. or lower, said process comprising:
  forming an aqueous acidic protein solution including a particulate form of said animal muscle tissue and an aqueous liquid, wherein the solution has a pH less than about 3.5 and does not substantially degrade protein of said animal muscle tissue,
  centrifuging said aqueous acidic protein solution to form a protein rich aqueous phase and a nonaqueous phase containing membrane lipids,
  recovering said protein rich aqueous phase,
  ultrafiltering said protein rich aqueous phase to form a retentate containing myosin protein and actin protein, and
  recovering said retentate, wherein said retentate comprises the low salt protein solution.

2. The process of claim 1 wherein said pH of said protein rich aqueous liquid solution is between about 2.5 and about 3.5.

3. The process of any one of claim 1 or 2 wherein said animal muscle tissue is fish muscle tissue.

4. The process of any one of claim 1 or 2 wherein said animal muscle tissue is poultry muscle tissue.

5. The process of any one of claim 1 or 2 wherein said animal muscle tissue is beef muscle tissue.

6. A process for recovering a low salt protein solution derived from animal muscle tissue, said solution being characterized as containing between about 1.9 and 25 weight % protein based on the weight of the solution, having a protein to salt weight ratio greater than about 35, and wherein said solution does not form a gel when heated to a temperature of 55° C. or lower, said process comprising:
  forming an aqueous acidic protein solution including a particulate form of said animal muscle tissue and an aqueous liquid, wherein the solution has a pH less than about 3.5 and does not substantially degrade protein of said animal muscle tissue,
  ultrafiltering said aqueous acidic protein solution to form a retentate containing myosin protein and actin protein, and
  recovering said retentate, wherein said retentate comprises the low salt protein solution.

7. The process of claim 6 wherein said pH of said protein rich aqueous liquid solution is between about 2.5 and about 3.5.

8. The process of any one of claim 6 or 7 wherein said animal muscle tissue is fish muscle tissue.

9. The process of any one of claim 6 or 7 wherein said animal muscle tissue is poultry muscle tissue.

10. The process of any one of claim 6 or 7 wherein said animal muscle tissue is beef muscle tissue.

11. A process for forming a pasteurized protein solution derived from animal muscle tissue, wherein said solution is capable of forming a gel at a temperature of about 40° C. or lower, said process comprising:
  forming an aqueous acidic protein solution including a particulate form of said animal muscle tissue and an aqueous liquid, wherein the solution has a pH less than about 3.5 and does not substantially degrade protein of said animal muscle tissue,
  centrifuging said aqueous acidic protein solution to form a protein rich aqueous phase and a nonaqueous phase containing membrane lipids,
  recovering said protein rich aqueous phase,
  forming a low salt protein solution which has a salt concentration sufficiently low so that gelation does not occur at temperatures of 55° C. or lower by either (i) ultrafiltering said protein rich aqueous phase to form a retentate containing myosin protein and actin, or (ii) adding a solid or gel protein composition derived from animal muscle tissue to said protein rich aqueous phase,
  heating or irradiating said low salt protein solution to inactivate microorganisms in said low salt protein solution thereby to form a pasteurized protein solution, and
  adding a sufficient amount of a physiologically acceptable salt to said pasteurized protein solution so that said pasteurized protein solution forms a gel at temperatures of about 40° C. or lower.

12. A process for forming a pasteurized protein solution derived from animal muscle tissue, wherein said solution is capable of forming a gel at a temperature of about 40° C. or lower, said process comprising:

forming an aqueous acidic protein solution including a particulate form of said animal muscle tissue and an aqueous liquid, wherein the solution has a pH less than about 3.5 and does not substantially degrade protein of said animal muscle tissue, forming a low salt protein solution which has a salt concentration sufficiently low so that gelation does not occur at temperatures of 55° C. or lower by either (i) ultrafiltering said protein rich aqueous solution to form a retentate containing myosin protein and actin protein, or (ii) adding a solid or gel protein composition derived from animal muscle tissue to said protein rich aqueous solution, heating or irradiating said low salt protein solution to inactivate microorganisms in said low salt protein solution thereby to form a pasteurized protein solution, and adding a sufficient amount of a physiologically acceptable salt to said pasteurized protein solution so that said pasteurized protein solution forms a gel at temperatures of about 40° C. or lower.

13. The process of any one of claim 11 or 12 wherein said pH of said protein rich aqueous liquid solution is between about 2.5 and about 3.5.

14. The process of any one of claim 11 or 12 wherein said animal muscle tissue is fish muscle tissue.

15. The process of any one of claim 11 or 12 wherein said animal muscle tissue is poultry muscle tissue.

16. The process of any one of claim 11 or 12 wherein said animal muscle tissue is beef muscle tissue.

17. The process of any one of claim 11 or 12 comprising the further step of drying said pasteurized protein solution to form a pasteurized protein powder.

18. The process of claim 13 comprising the further step of drying said pasteurized protein solution to form a pasteurized protein powder.

19. The process of claim 14 comprising the further step of drying said pasteurized protein solution to form a pasteurized protein powder.

20. The process of claim 15 comprising the further step of drying said pasteurized protein solution to form a pasteurized protein powder.

21. The process of claim 16 comprising the further step of drying said pasteurized protein solution to form a pasteurized protein powder.

* * * * *